United States Patent [19]

Osterholm

[11] 4,445,514
[45] May 1, 1984

[54] EXTRAVASCULAR CIRCULATION OF OXYGENATED SYNTHETIC NUTRIENTS TO TREAT TISSUE HYPOXIC AND ISCHEMIC DISORDERS

[75] Inventor: Jewell L. Osterholm, Radnor, Pa.

[73] Assignee: Thomas Jefferson University, Philadelphia, Pa.

[21] Appl. No.: 275,117

[22] Filed: Jun. 18, 1981

Related U.S. Application Data

[62] Division of Ser. No. 139,886, Apr. 14, 1980, Pat. No. 4,378,797.

[51] Int. Cl.³ .................. A61K 31/00; A61M 5/14
[52] U.S. Cl. .................................................. 128/632
[58] Field of Search .................. 128/1 R, 630, 768, 632

[56] References Cited

U.S. PATENT DOCUMENTS

| | | | |
|---|---|---|---|
| 3,516,410 | 6/1970 | Hakim | 128/350 |
| 3,583,387 | 6/1971 | Garner | 128/1 |
| 3,626,950 | 12/1971 | Schulte | 128/350 |
| 3,669,094 | 6/1972 | Heyer | 128/2 |
| 3,669,116 | 6/1972 | Heyer | 128/350 |
| 3,690,323 | 9/1972 | Wortman et al. | 128/350 |
| 3,753,865 | 8/1973 | Belzer | 195/127 |
| 3,823,091 | 7/1974 | Samejima | 252/312 |
| 3,894,541 | 7/1975 | El-Shafei | 128/350 |
| 3,941,119 | 3/1976 | Corrales | 128/2 |
| 3,946,731 | 3/1976 | Lichtenstein | 128/214 |
| 3,989,843 | 11/1976 | Chabert et al. | 424/325 |
| 4,110,474 | 8/1978 | Lagow et al. | 424/350 |
| 4,148,314 | 4/1979 | Yin | 128/214 |
| 4,163,734 | 4/1979 | Sorensen et al. | 252/408 |
| 4,173,224 | 11/1979 | Marx et al. | 128/214 |
| 4,173,654 | 11/1979 | Scherer | 424/350 |

OTHER PUBLICATIONS

Fritschka et al., "Total and Regional Cerebral Blood Flow During Perfusion from the Lateral Ventricle to the Cisterna Magna in Conscious Dog: Effect of Hemorrhagic Hypotension and Retransfusion on Cerebral Blood Flow", Circulatory Shock 7:333-342, (1980).
Rodnight, R., Biochemistry Journal, vol. 57, p. 661.
Clark et al., Science, vol. 152, pp. 1755-1756, (1966).
Gollon, F. et al., Alabama Journal of Medical Science, vol. 4, p. 336, (1967).
Gollon, F. et al., The Physiologist, vol. 9, p. 191, (1966).
Sloviter, H. A. et al., Nature, (London), vol. 216, p. 458, (1967).
Geyer, R. P., Federation Proceedings, vol. 29, No. 5, Sep.-Oct., 1970.
Geyer, R. P., Med u Ernohn, vol. 11, p. 256, (1970).
Krone, W. et al., Biochemika et Biophysica Acta, vol. 372, pp. 55-71, (1974).
Rosenblum, W. I., "Fluorocarbon Emulsions and Cerebral Microcirculation," Federation Proceedings, vol. 34, No. 6, p. 1493, (May, 1975).
Kontos, H. A. et al., "Role of Tissue Hypoxemia in Local Regulation of Cerebral Microcirculation," American Journal of Physiology, vol. 363, pp. 582-591, (1978).
Hare et al., "Rapid and Sensitive Ion-Exchange Fluorometric Measurement of G-Aminobutyric Acid in Physiological Fluids", Anal. Biochem., vol. 101, pp. 349-355, (1980).
Navari et al., Res. Exp. Med., vol. 170, pp. 169-180, (1977).
Clark et al., Fed. Proc., vol. 34, pp. 1468-1477, (1979).
Osterholm, J. L., Pathophysiology of Spinal Cord Injury, C. C. Thomas, Springfield, Illinois, (1978).
Pappenheimer, J. R. et al., "Perfusion of the Cerebral Ventricular System in Unanesthized Goats," Am. J. Physiol., vol. 203, No. 5, pp. 763-774, (1962).
Sklar, Frederick H. et al., "Recirculatory Spinal Subarachnoid Perfusions in Dogs: A Method for Determining CSF Dynamics Under Non-Steady State Conditions," Neurosurgery, vol. 1, No. 1, pp. 48-56, (1977).
Sloviter, Henry A. et al., "Erythrocyte Substitute for Perfusion of Brain," Nature, vol. 216, pp. 458-460, (Nov. 4, 1967).
Hansebout, Robert R. et al., "Oxygenated Fluorocarbon Perfusion as Treatment of Acute Spinal Cord Compression Injury in Dogs," J. Neurosurg., vol. 55, pp. 725-732, (1981).
Siegel et al., Basic Neurochemistry, 2d Little Brown Boston, (1978), p. 297.
Astrup, et al., "The Increase in Extravellular Potassium Concentration in The Ischemic Brain in Relation to the Preischemic Functional Activity and Cerebral Metabolic Rate", Brain Research, 199:161-174, (1980).

Ames et al., "Cerebral Ischemia: II. The No-Reflow Phenomenon", Am. J. Pathol., vol. 52, No. 2, pp. 437–448, (1968).

Berkenbosch et al., "Influence of the CSF Bicarbonate Concentration on the Ventilatory Response to $CO_2$ in Relation to the Location of the Central Chemoreceptors", Respiration Physiology, 35:215–236, (1978).

Britton et al., "Effect of Cerebral Extracellular Fluid Acidity on Total and Regional Cerebral Blood Flow", Journal of Applied Phys., vol. 47, pp. 818–826, Oct.–Dec., (1979).

Brown et al., "Fluorocarbon Sonicated as a Substitute for Erythrocytes in Rat Liver Perfusion", Surgery, vol. 71, No. 3, pp. 388–394, (Mar. 1972).

Callaghan et al., "CSF Perfusion to Treat Intraventricular Penicillin Toxicity", Arch. Neurol., vol. 38, pp. 390–391, (1981).

Carey et al., "The Effect of Severe Hypoglycemia Upon Cerebrospinal Fluid Formation, Ventricular Iodide Clearance, and Brain Electrolytes in Rabbits", J. Neurosurg., vol. 54, pp. 370–379, (1981).

Chiang et al., "Cerebral Ischemia: Vascular Changes", American Journal of Pathology, vol. 52, pp. 455–476, (1968).

Clark et al., "Can Fluorocarbon Emulsions Be Used as Artifical Blood?", Triangle, vol. 11, No. 4, pp. 115–122, (1972).

Curtis, C., "Blood and Money", Forbes, pp. 100–102, (Nov. 9, 1981).

Dirks et al., "Fluorocarbon Perfusion Medium Applied to the Isolated Rat Brain", Journal of Pharmacological Methods, 4:95–108, (1980).

Fischer et al., "Reassessment of Cerebral Capillary Changes in Acute Global Ischemia and Their Relationship to the 'No-Reflow Phenomenon'", Stroke, vol. 8, pp. 36–39, (1977).

Fischer, E., "Impaired Perfusion Following Cerebrovascular Stasis", Arch Neurol, vol. 29, pp. 361–366, (Dec. 1973).

Primary Examiner—George F. Lesmes
Assistant Examiner—Nancy A. B. Swisher
Attorney, Agent, or Firm—Woodcock, Washburn, Kurtz, Mackiewicz & Norris

[57] ABSTRACT

A novel system and method for treating ischemic neurologic tissue is disclosed wherein an oxygenated nutrient emulsion is circulated through at least a portion of the cerebospinal pathway. The nutrient emulsion contains an oxygenatable non-aqueous component, an aqueous nutrient component, an emulsification component, and other components which render physiologic acceptability of the nutrient emulsion. Methods for producing the nutrient emulsion and a system for delivering that emulsion to the cerebrospinal pathway are also disclosed. Additionally, novel diagnostic methods for diagnosing the physiologic state of hypoxic-ischemic and other diseased neurologic tissue during treatment are provided.

26 Claims, 3 Drawing Figures

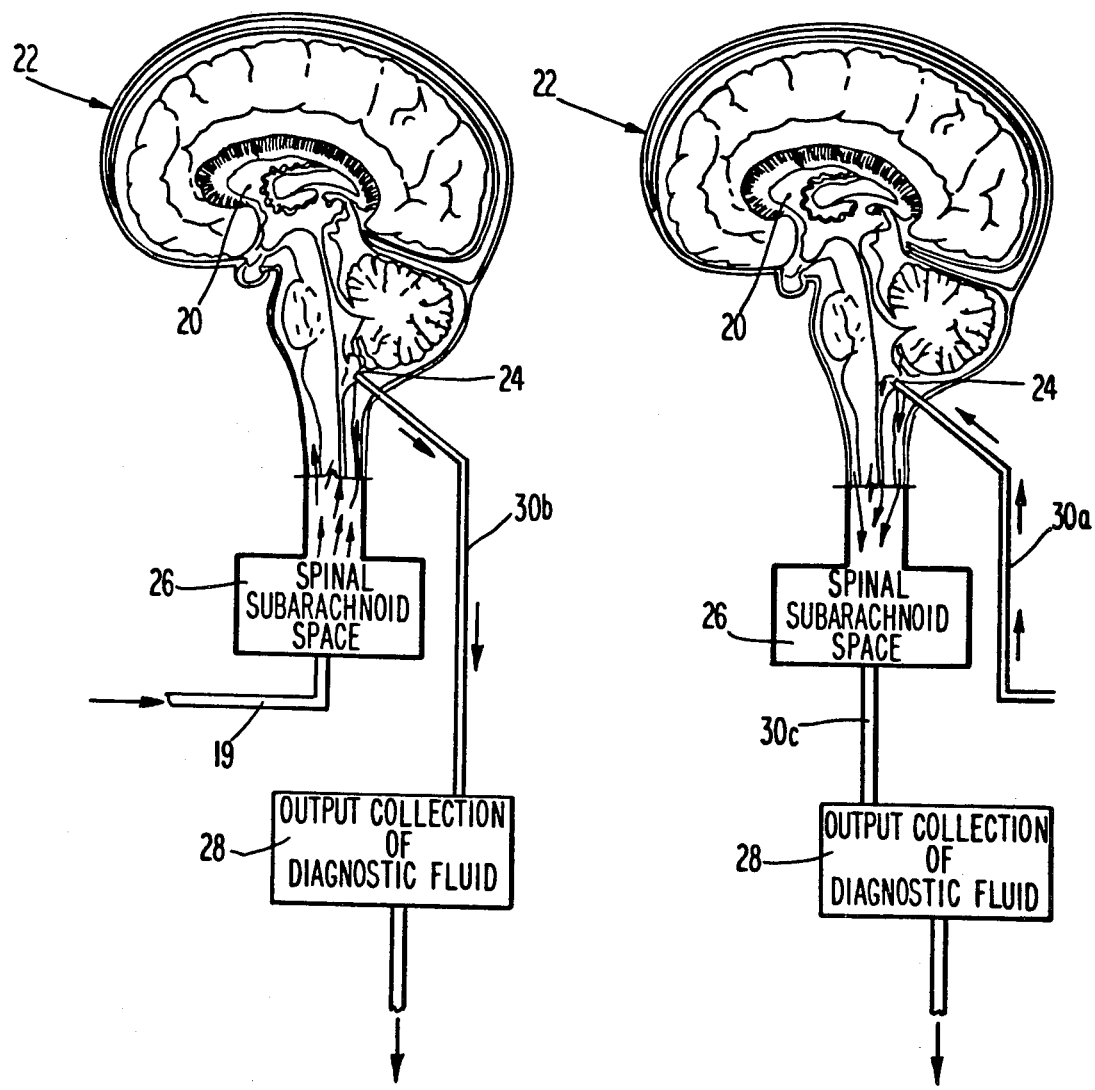

EXTRAVASCULAR CIRCULATION OF OXYGENATED SYNTHETIC NUTRIENTS TO TREAT TISSUE HYPOXIC AND ISCHEMIC DISORDERS

This is a division, of application Ser. No. 139,886, filed Apr. 14, 1980, now U.S. Pat. No. 4,378,797.

BACKGROUND OF THE INVENTION

Cerebrovascular accident, a disease commonly known as "stroke" remains a leading cause of death and probably constitutes the single largest category of long term disability in this country. In spite of current medical knowledge and available treatments, a major central nervous system vascular occlusion is attended by irreversible damage to the affected brain region(s). A "completed stroke" is manifest by a fixed and permanent neurological deficit. Millions of dollars have been expended in stroke research and care by Federal and private agencies without a single substantial gain in our present chemotherapeutic abilities for a completed stroke. On a clinical level, once vascular flow in any portion of the central nervous system has ceased for longer than a few minutes, a permanent "stroke" invariably follows. Accordingly, a long felt need exists to prevent permanent damage and/or reverse neurologic deficits resulting from interrupted vascular flow.

Over the years, many experiments have been conducted with materials possessing high oxygen-dissolving properties, many of which have been incorporated as constituents in "artificial blood". The concept of utilizing materials possessing high oxygen-dissolving properties for the maintenance of tissue respiration was first reported by Rodnight in 1954. See Rodnight, R.; Biochemistry Journal, Vol 57, pg. 661. Rodnight capitalized upon the considerable oxygen solubility found in silicone oils, and sustained tissue slices by incubation in these oxygen laden oils. Approximately 12 years later, Clark reported experiments involving the total immersion of small animals in silicone oils and fluorocarbon liquids. Rats totally immersed in oxygenated silicone oil survived for one hour with no apparent ill effects, but died several hours after removal, from unknown causes. Similar experiments using synthetic fluorocarbon liquids, which dissolve about 3 times more oxygen than do the silicone oils, were performed with some success. Under these conditions, animals survived immersion in oxygenated synthetic fluorocarbon liquids and thereafter returned to apparent health. See Clark, L. C. Jr. and Gollon, F.: *Science*, Vol. 152, pg. 1755, (1966); and Gollon, F., Clark, L. C. Jr.,: *Alabama Journal of Medical Science*, Vol. 4, Pg. 336, (1967). While arterial oxygenation was reported as excellent for Clark's studies in rats, coincident impairment of carbon dioxide elimination was also reported, as was pulmonary damage from breathing flourocarbon liquids. One rat, which was observed for five days following liquid breathing, was described as being in respiratory distress and as succumbing within 15 minutes after the sub-cutaneous administration of hydrocortisone (50 mg), with copious loss of body fluid from the trachea. In this regard, Clark concluded:

These organic liquids should prove to be of value in studies of gas exchange in living tissues in animals. Organic liquids, since they can support respiration with oxygen at atmospheric pressure and have other unique qualities, may find use in submarine escape, undersea oxygen support facilities, and medical application. The pulmonary damage caused by the breathing of the organic liquids available at the present time remains a major complication of their use in man. *Science*, Vol. 152, pg. 1756.

Following these observations, fluorocarbon liquids were used as an incubation medium for isolated rat hearts. See Gollan and Clark, *The Physiologist*, Vol. 9, pg. 191, (1966). In this work, myocardial oxygen requirements were apparently well met, however these hearts did not flourish without intermittent fluorocarbon removal and washing with oxygenated, diluted blood. This phenomen has been explained in terms of aqueous phase lack in pure fluorocarbons such that necessary ionic exchange is impeded.

More recently, considerable attention has been directed to the use of fluorocarbons as constituents of artificial blood. Sloviter, in order to overcome the problem of aqueous-metabolite fluorocarbon insolubility, made an emulsion with fluorocarbon and albumin. Sloviter's emulsion sustained the isolated rat brain by a vascular perfusion as well as did an erythrocyte suspension. See Sloviter, H. A. and Kamimoto, T.: *Nature* (London), Vol. 216, Pg. 458, (1967). A better emulsion was later developed comprising a detergent, "Pluronic F 68" (manufactured by the Wyandotte Chemical Corp., Wyandotte, Mich.), and fluorocarbon liquids which were properly emulsified using sonic energy. This improved emulsion permitted the replacement of most of the blood of a rat which was then reported as surviving in an atmosphere of oxygen for five to six hours. See Geyer, R. P.: *Federation Proceedings*, Vol. 29 No. 5, September-October, 1970; and Geyer, R. P.: *Med u Ernohn*, Vol. 11, Pg. 256, (1970).

Experiments have also been reported wherein fluorocarbons have been used to perfuse livers. Ten hours after in vitro fluorocarbon perfusion, the isolated liver ATP; AMP; lactate/pyruvate ratio; and a number of other metabolites were found to be as good or better than livers perfused in vitro with whole blood. See Krone, W., Huttner, W. B., Kampf, S. C., et al.: *Biochemika et Biophysica Acta*, Vol. 372, Pgs. 55–71, (1974). These detailed metabolic studies indicated that the organs perfused with 100% fluorocarbon liquid were redeemed "intact"; while only 75% of the whole blood infused organs maintained a similar degree of metabolic integrity. The ability of fluorocarbon perfusion to maintain cellular integrity was confirmed by electron-microscopy studies. The cells had normal mitochondrial ultra structure after ten hours of fluorocarbon support, indicating the persistence of normal or adequate aerobic metabolism.

Fluorocarbons have also been used in experiments involving cerebral blood circulation. In Rosenblum's studies, mouse hematocrits were reduced to 10-15 by exchanging the animal's blood with a fluorocarbon solution. When the animals were respired with 100% oxygen after intravascular fluorocarbon infusions, the brains remained metabolically sound. These organs were able to reverse rising NADH levels and EEG abnormalities induced by short period nitrogen inhalation. The EEG's of fluorocarbon treated animals could be activated by the central nervous system stimulant metrazole. By these criteria, intravascular fluorocarbon does support the cerebral microcirculation and provides functions of oxygenation, metabolism and electrical activity which are normally associated with blood transport. Please refer to Rosenblum, W. I.; "Fluorocarbon Emulsions and Cerebral Microcirculation", *Federation Proceedings*, Vol. 34, No. 6, Pg. 1493, (May 1975).

As reported by Kontos et al., the marked vasodilation of small cerebral surface arteries which occurs in response to acute profound hypoxemia may be locally obviated by perfusing oxygen equilibrated fluorocarbon into the space under the cranial window. See Kontos, H. A., et al., "Role of Tissue Hypoxemia in Local Regulation of Cerebral Microcirculation", *American Journal of Physiology*, Vol. 363, Pgs. 582–591, (1978). Kontos et al. described the effect of perfusions with fluorocarbon with 100% oxygen as resulting from increased supplies of oxygen to the neural cells and consequent partial or complete relief of hypoxia, rather than to a local increase in the oxygen tension in the immediate environment of the vascular smooth muscle of the pial arterioles. Two other potential explanations for the observed action are suggested in the Kontos et al. article.

In 1977, Doss, Kaufman and Bicher reported an experiment wherein a fluorocarbon emulsion was used to partially replace cerebrospinal fluid with the intention of evaluating its protective effect against acute anoxia. According to this experiment, systemic hypoxia was produced through one minute of 100% nitrogen inhalation. A bolus of oxygenated fluorocarbon placed in the cisterna magna immediately prior to nitrogen breathing increased regional cerebrospinal fluid $O_2$ tension by a factor of 5. During the one minute experimental period, the fluorocarbon emulsion provided twice as much brain tissue oxygen as was found in saline injected controls. Doss et al. found the anticipated regional tissue oxygenation decline attending nitrogen inhalation to be halved by the administration of the oxygen bearing fluorocarbon emulsion.

In spite of the above described experiments, there has yet to be any reported information of a practical therapeutic approach to the treatment of ischemic tissue, and particularly human ischemic central nervous system disease.

SUMMARY OF THE INVENTION

The present invention provides a novel nutrient formulation for circulation through cerebrospinal fluid pathways, and systems and methods for using same to treat central nervous tissue hypoxic-ischemic conditions. Through its use, a new diagnostic methodology is also disclosed.

The cerebrospinal fluid (CSF) pathway system, which intimately bathes and permeates brain and spinal cord tissues, constitutes a unique anatomical relationship within the body. Although it has some similarities to systemic lymphatics, its anatomical arrangement differs considerably from that of lymph. Indeed, this system has been named the "third circulation". Due to the extensive area of CSF-tissue contact over the cerebral and cord surfaces, in the miniature Virchow-Robins spaces, and cerebral ventricles, the cerebrospinal fluid system constitutes a vast, complex and intimate therapeutic avenue for access to central nervous tissue. Excepting certain infections and neoplasms where the cerebrospinal fluid is now utilized as an an a treatment conduit, the cerebrospinal fluid system has not been otherwise widely exploited as an easily accessible therapeutic route and has never been used as a continuous therapeutic diagnostic circulation system in man. The present invention is predicated on the recognition that, when regional cerebral blood flow is interrupted, such as after major stroke, or is otherwise seriously impeded by profound vaso-spastic states, the cerebrospinal fluid pathway actually represents the only practical and viable anatomical route by which these tissues may be readily treated. This results from the fact that the usual vascular delivery system is either occluded or non-functional, and thus tissues within affected territories cannot be properly served.

In accordance with the present invention, essential cellular substrates are delivered to beleaguered ischemic brain regions by utilizing the "back door" cerebrospinal fluid delivery route. Accordingly, the present invention provides a novel nutrient emulsion, circulatory method and system which provide necessary nutrient penetration into regions suffering vascular deprivation.

It has been found that the cerebrospinal fluid to brain relationship is not characterized by the rigid and highly selective barrier mechanisms which are present at the blood-brain interface. Thus, the penetration rate of materials from cerebrospinal fluid regions to the brain relate largely to molecular size, that is, small substances penetrate deeply while large molecules move more slowly into brain substance. Although entry rates are generally inversely proportional to molecular weight, penetration is also influenced by lipid solubility and the molecular configuration of the penetrating substance. Accordingly, the present invention provides a nutrient emulsion containing essential brain nutrients including selected electrolytes, having a relatively low molecular size which, in accordance with the methods of the present invention, are caused to relatively freely diffuse from either the ventricular or subarachnoid fluid regions into the brain matter to be treated. Accordingly, the present invention provides a novel nutrient emulsion which has been purified, balanced, and perfected to fall within the narrow physiologic limits while nonetheless providing the desired nutritional characteristics referred to above.

In accordance with the preferred embodiment of the present invention, this nutrient emulsion constitutes "synthetic cerebrospinal fluid" comprising pre-selected electrolytes, glucose, amino acids, at least one oxygen-carrying component, typically a fluorocarbon, and other components which impart to the composition a pre-selected pH, buffering capability, and osmolarity. This nutrient emulsion is prepared by controlling sonication time and by properly dialyzing the material to achieve a toxic free emulsion. The resulting solution may be rapidly oxydated to $O_2$ pressures of 650 mm of mercury by simply bubbling 100% oxygen gas through at atmospheric pressures. In a covered glass container, the resultant nutrient emulsion will not appreciably decline in its $pO_2$ for at least two hours. As a result, a novel oxygenated nutrient emulsion is provided which is believed to exhibit exceptional therapeutic properties.

The present invention also provides a novel method and apparatus for circulating the oxygenated nutrient emulsion through cerebral spinal fluid pathways, particularly those pathways which contact brain and spinal cord tissue. According to these methods, treated tissues exhibit a substantially improved ability to resist and/or repair damage which would otherwise result from vascular occlusion. In accordance with the preferred method of the present invention, the novel oxygenated nutrient emulsion is circulated through this cerebrospinal fluid route by injecting it into brain ventricles and withdrawing it from the cisterna magna (as shown in FIG. 1, via withdrawal means 30) the spinal subarachnoid space (as shown in FIG. 1, via withdrawal means 30b) to nourish and to treat central nervous tissues. In other instances the fluid may be injected into the subarachnoid space and withdrawn from another subarachnoid position (as shown in FIG. 2). The preferred embodiment oxygenated nutrient emulsion should be circulated to tissues to be treated in amounts sufficient to provide adequate gas exchange. Pure fluorocarbon may contain 50 ml $O_2$ per 100 ml at one atmosphere oxygen while normal blood contains only 20 ml $O_2$/100 ml under the same conditions. The oxygen carrying capability per ml of the final emulsion is considerably less than that of pure fluorocarbon by reason of its content of other constituents for normalizing osmotic pressure, buffering, electrolytes, and other physiologic balancing materials. Thus, the preferred embodiment nutrient emulsion may be charged with oxygen (100% $O_2$ at one atmosphere) to attain $pO_2$ tensions of 650–700 ml of mercury and an $O_2$ content of 20 ml per 100 ml. Under rapid circulation conditions, the integral $O_2$ exchange (fluorocarbon to tissue) has been found to be about 50%. Thus, an oxygen exchange value of ten (10) $O_2$/100 ml nutrient emulsion is provided by the present method.

In accordance with the preferred embodiment of the present invention, sufficient nutrient emulsion should be supplied to counteract oxygen deprivation to the affected tissue. For example, the entire supertentorial adult cat brain weighs 12 grams (plus or minus 2) and the normal metabolic consumption of oxygen of the cat brain equals 3–4 ml per 100 grams per minute. This total metabolic need may be met with the circulation rate of 6–8 mls per minute. Metabolic needs necessary to simply sustain and/or salvage tissue can be achieved by perfusion rates of one half or less of this optimum. Within these constraints an easily achieved sustenance flow rate of 20 ml/minute would be anticipated to salvage 100 gms of human brain tissue. It has been found experimentally that it is possible to supply sufficient oxygen to counteract the deprivation of the affected tissue through circulation of the nutrient emulsion through the cerebrospinal fluid route. In fact, under carefully controlled conditions, it is believed within the scope of the present invention to nourish the entire human brain using the preferred embodiment apparatus, method and substance of the present invention. In this manner, central nervous neurons deprived of major blood supply may be sustained without significant damage.

In accordance with the preferred embodiment of the present invention, a novel system is disclosed for administering and maintaining the oxygenated nutrient emulsion for delivery and circulation through the cerebrospinal route.

The preferred embodiment system of the present invention effectively carries out the circulation and equilibration of the nutrient emulsion during treatment. This system, which is diagrammatically illustrated in FIG. 1, generally comprises a reservoir containing nutrient emulsion; means for delivering the nutrient emulsion at pre-selected flow rates; an oxygenation means for equilibrating the nutrient emulsion to desired gaseous tension levels; heat exchanger and/or cooling unit means for selectively controlling the temperature of the nutrient emulsion; filtering means for cleansing the nutrient emulsion; and circulation monitoring means for insuring that desired circulation flows and pressures are maintained within the system.

The present invention also provides a method of diagnosing conditions of neurologic tissue in mammals. This novel method generally comprises providing an artificial spinal fluid of known composition, injecting that artificial spinal fluid into at least a first portion of the cerebrospinal pathway of a mammal, withdrawing a diagnostic fluid from a second portion of that pathway to create a circulation of fluid at least through a portion of said pathway, monitoring the composition of said diagnostic fluid, and comparing for at least a selected difference in the compositions of said artificial spinal and diagnostic fluids, whereby the detected differences in those compositions are at least diagnostic of neurologic tissue disposed along said portion of the cerebrospinal pathway. In accordance with the diagnostic methods of the present invention, the diagnostic fluids may be monitored for differences in oxygen content, lactic acid concentration, carbon dioxide concentration, potassium and/or sodium ion concentration, enzyme concentration, pH difference, ammonium concentrations, GABA (gamma-aminobutyric acid) and other amino acid(s) concentrations, microorganism content, bacterial count, myelin fragments, cellular fragments or organelles, malignant cells, and/or poisons.

It is also within the scope of the present invention to provide a novel nutrient liquid and/or diagnostic liquid for treating cerebrospinal tissue containing various novel specified components which is formulated using novel methodology.

It is additionally within the scope of the present invention to provide a novel apparatus for treating patients having ischemic-hypoxic tissues, including novel injection means (20a or 30a) and withdrawal means (30, 30b or30c) comprising a novel catheter means which is particularly adapted for injecting oxygenated nutrient liquid into a cerebral ventricle without danger of substantially damaging neurologic tissue in the vicinity of that ventricle.

In addition to the methods described above, it is within the scope of the present invention to provide additional therapeutic agents to the nutrient emulsion, such as antineoplastic agents; antibiotics, and/or other therapeutic agents for use in treating the target tissue(s).

Accordingly, the primary object of the present invention is the provision of a method, substance, and system for providing early stroke treatment.

Other objects of the present invention are to provide treatments for brain and spinal cord injuries, cerebral hemorrhage, cerebral vasospasm, senility, after general hypoxia and other hypoxia-ischemic related neurological disorders.

It is a further object of the present invention to provide therapeutic treatment which may sustain the life of the brain and central nervous system tissues in case of profound shock and/or temporary cardio-respiratory failure.

It is a further object of the present invention to provide life-sustaining support to the brain and/or spinal cord tissues during the conduct of neurological or cardiovascular surgery.

Other objects of the present invention are the provision of methods which may compliment treatments of central nervous system neoplasms by either external radiation and chemotherapy by providing local tissue hyperoxygenation or drug which may enhance drug or radiation tumorocidal effects.

Further objects of the present invention include the provision of methods which are useful in treating anoxic states attending birth injury. The present method will also assist in removal of central nervous system poisons.

These and other objects of the present invention will become apparent from the following more detailed description.

BRIEF DESCRIPTION OF THE DRAWINGS

FIG. 2 is a diagrammatic view of a portion of the preferred embodiment treatment system of FIG. 1 illustrating an alternate circulation route wherein oxygenated nutrient emulsion is injected into the spinal subarachnoid space and is collected from the cisterna magna;

FIG. 3 is a diagrammatic view of a portion of the preferred embodiment treatment system illustrated in FIG. 1 showing an alternate circulation route wherein oxygenated nutrient emulsion is injected into the cisterna magna for passage through the spinal subarachnoid space for withdrawal from a lumbar region.

DESCRIPTION OF THE PREFERRED EMBODIMENTS

Figure 1:
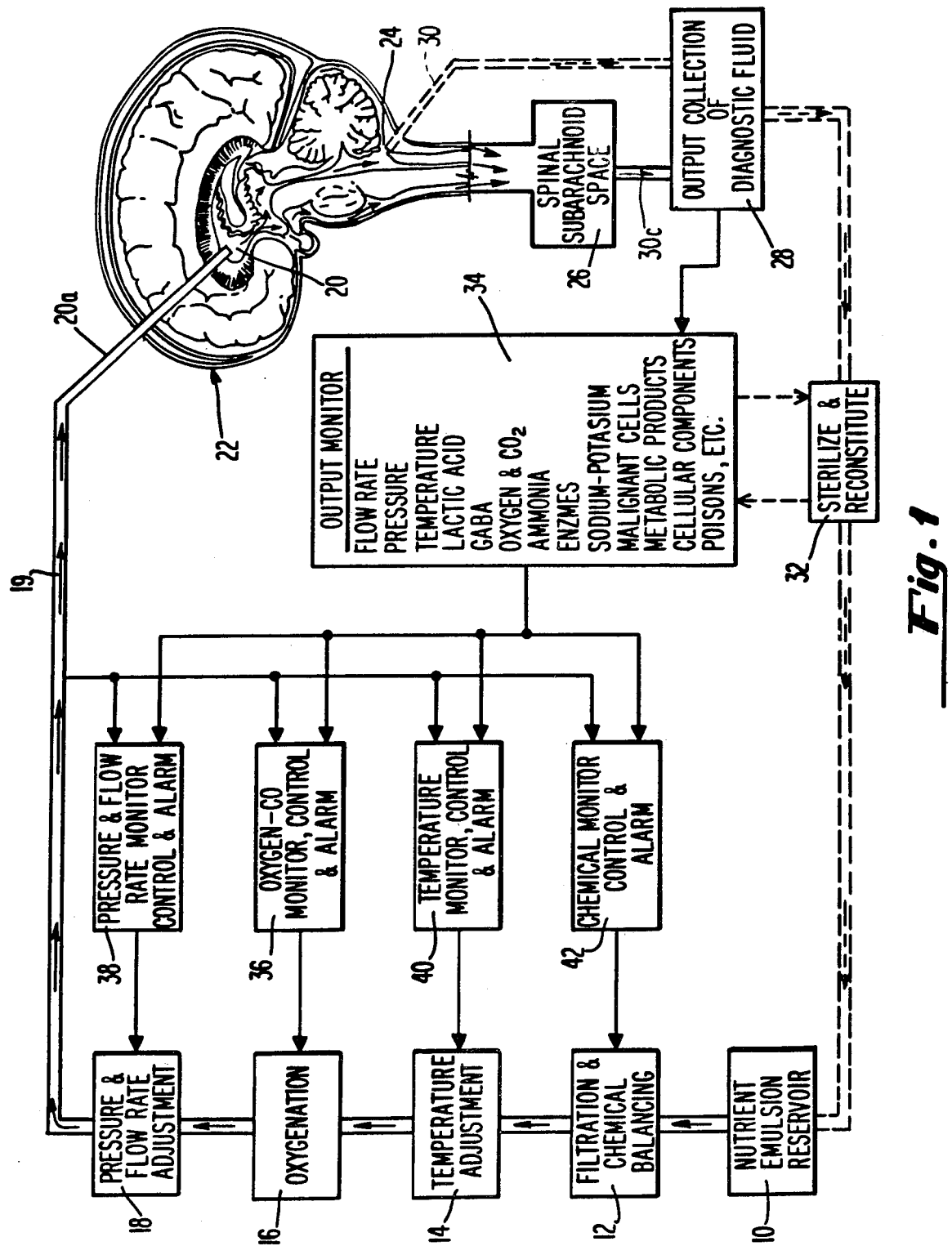
FIG. 1 is a diagrammatic view of the preferred embodiment treatment system of the present invention illustrating the circulation of nutrient emulsion from a reservoir, into a cerebral ventricle, such as a lateral ventricle, through a portion of the cerebrospinal fluid pathway for output from the spinal subarachnoid space or from the cisterna magna.

In the following more detailed description, numerous examples have been selected for the purpose of explanation and illustration of the preferred embodiments of the present invention. One of ordinary skill in the art will readily recognize that numerous substitutions or alterations from the examples set forth may be made without departing from the spirit of the present invention, which is defined more particularly in the appended claims.

Referring now to FIG. 1, the preferred system for circulating nutrient emulsion through a cerebrospinal pathway is diagrammatically illustrated. As shown in FIG. 1, a nutrient emulsion reservoir 10 is provided for receiving and retaining nutrient emulsion, the preparation of which will be described more fully hereinafter. In accordance with the preferred system and method of the present invention, the nutrient emulsion is injected into a cerebrospinal pathway following pH adjustment and filtering, temperature adjustment, oxygenation, and adjustment of the pressure and flow rate of the nutrient input stream 19. In FIG. 1, these steps are illustrated diagrammatically at 12, 14, 16 and 18 respectively. Preferably, the nutrient input stream 19 is delivered to a ventricle of the brain, and more particular to a lateral ventricle 20 of the human brain designated generally 22. Injection of the nutrient input stream permits the oxygenated nutrient emulsion to come into contact with the subarachnoid spaces, miniature Virchow-Robins spaces, cerebral and cord surfaces, and cerebral ventricles. For the system illustrated in FIG. 1, the nutrient input stream 19 is diagrammatically illustrated as being injected into a lateral ventricle 20. Since the lateral ventricle is in fluid communication with other portions of the cerebrospinal pathway, the withdrawal of fluid from a portion of the pathway which is remote from that ventricle will create a circulation of fluid within the cerebrospinal pathway. More particulary, circulation of the nutrient input stream through at least a portion of the cerebrospinal pathway may be accomplished by withdrawing fluid (via withdrawal means 30c) from the spinal subarachnoid space, diagrammatically illustrated as 26 in FIG. 1, or alternatively, from the cisterna magna 24 (via withdrawal means 30 or 30b.)

As illustrated in FIG. 1, circulation of fluid through the cerebrospinal pathway is intended to permit the treatment of at least cerebral tissue. It is within the scope of the present invention, however, to focus treatment on selected neural tissue areas, in which case alternative points of injection and withdrawal of fluid may be selected by the attending physician. For example, in the case of spinal cord injury, it is anticipated that the point of injection of oxygenated nutrient emulsion may preferably be in the lumbar, spinal subarachnoid space, with the point of withdrawal being at the cisterna magna. See FIG. 2. While the above mentioned cerebrospinal pathway injection and withdrawal points are preferred, it is within the scope of the present invention to utilize other injection and withdrawal locations, provided a substantial circulation of fluid through the area of affected neurologic tissue is established by utilizing the selected loci. As shown in FIG. 3, injection via injection means 30a into the cisterna magna and withdrawal via withdrawal means 30c from the spinal subarachnoid space is also possible.

The preferred injection means of the present invention comprises a cerebral catheter means 20a for insertion into a brain ventricle. This injection means comprises means for preventing a portion of the catheter located within a brain ventricle from damaging tissues surrounding the ventricle. In the preferred embodiment, an inflatable balloon tip may be provided for this purpose. The actual injection of nutrient emulsion into the brain ventricle is accomplished by providing an arrangement of the outlet holes disposed as series of slits radially spaced around the catheter tip. Both the injection means and withdrawal means also further comprise attachment means for attaching the catheter to the body in the vincinity of the injection or withdrawal sites. Thus the injection catheter may comprise a means for fixing at least a portion thereof with respect to the skull to insure catheter stability. The withdrawal catheter, which may have a tip with multiple perforations disposed therein, further comprises means for attaching at least a portion thereof to tissue in the region of the subarachnoid space. This attachment means may include a staple for attaching a non-collapsible portion of the catheter to a lumbar region of the skin.

It is not anticipated that the fluid which is withdrawn from the cerebrospinal pathway at the point of withdrawal will be identical in composition to the oxygenated nutrient emulsion which is injected at the injection point. By taking advantage of differences in composition which are detected in the withdrawn fluid, which may be considered to be a diagnostic fluid, the attending physician may easily monitor the physiologic condition of the neurologic tissue which is being treated. This diagnostic fluid may also be monitored to assure that treatment is proceeding according to plan. Accordingly, fluid which is withdrawn from the cerebrospinal pathway in directed to an output collection means 28 for collecting diagnostic fluid. Preferably, an output monitor 34 will continuously monitor various chemical and physical characteristics of the diagnostic fluid for such properties as flow rate, hydraulic pressure, potassium and sodium ion temperature, lactic acid concentration, gamma amino butyric acid and other amino acid concentrations, oxygen concentration, carbon dioxide concentration, enzymes, and ammonia concentration.

The output of this output monitor will not only provide the attending physician with information concerning the state of the cerebrospinal tissue being treated, but also will be fed back to the monitor, control and alarm systems for at least pressure and flow rate, temperature, oxygen-carbon dioxide and chemical constituency, as described more fully hereinafter. This diagnostic system takes advantage of the fact that ischemic neurologic tissue produces higher concentrations of such materials as Gamma-aminobutyric acid (GABA), lactate ion (lactic acid), enzymes and/or LDH (lactic dehydrogenase), ammonia, and other constituents which have been determined by analyzing cerebrospinal fluids of patents subjected by disease to similar anoxic conditions.* In accordance with the system of the present invention, however, a continuous monitoring of the state of neurologic tissue is possible, since the circulation of oxygenated nutrient emulsion will produce a continuous flushing of the affected tissues regions, and thus will result in diagnostic fluid component variations which are rapidly reflective of the physiologic state of the tissues being treated. Due to the multi-point injection-withdrawal method of the present invention, dangers which are inherent in sampling natural cerebrospinal fluid at a single location are avoided by utilizing a double venting method wherein the cerebrospinal fluid pressure is at all times carefully controlled.

*See for example, "Rapid and Sensitive Ion-Exchange Fluorometric Measurement of G-Aminobutyric Acid in Physiological Fluids", Hare et al., *Anal. Biochem.*, Vol. 101, 349-355 (1980) for a preferred GABA measurement method.

It is within the scope of the present invention to sterilize and reconstitute that diagnostic fluid as shown at step 32, whereupon that reconstituted diagnostic fluid may be provided as nutrient emulsion to the nutrient emulsion reservoir 10. As shown in FIG. 1, the output monitor 34 may monitor the diagnostic fluid during the sterilization and reconstitution processes and, if desired, ensure that the reconstituted fluid satisfies the requirements of the nutrient emulsion reservoir. As shown in FIG. 1, in order to ensure that appropriate degrees of oxygenation, filtration and chemical balancing, temperature adjustment, and pressure and flow rate are maintained, the nutrient input stream is monitored by various monitors, controls, and alarms, which are intended to provide a fail safe nutrient input stream. In particular, a pressure and flow rate monitor, control and alarm 38 is provided for monitoring the pressure and flow rate of the nutrient inut stream, for controlling the pressure and flow rate adjustment 18 to establish desired pressures and flow rates, and for sounding an alarm in the event that the nutrient input stream exceeds or falls below preselected pressures or flow rates. If desired, this alarm may additionally disable the pumping mechanism producing flow of the nutrient input stream such that the unit "shuts down" upon detection of unacceptable input stream conditions.

Referring now to the temperature monitor, control and alarm, the temperature characteristics of the nutrient input stream are similarly detected, at least to ensure that hyperthermic states except when used as therapeutic modality are avoided. While in most instances, the nutrient input stream will be adjusted to a 37° C. temperature, it may be desired to select hypothermic temperatures in order to establish certain treatment conditions. In either event, the temperature monitor will continuously detect the temperature of the input stream, will control the temperature adjustment 14 to establish a preselected temperature, and will sound an alarm and/or disable the system in the event that a preselected temperature range is not maintained in the nutrient input stream.

Referring now to the chemical monitor, control and alarm 42, the nutrient input stream will be continuously monitored for one or more chemical or physical characteristics of the nutrient input stream, and will control the chemical balancing, filtration, etc. which is performed by the filtration and chemical balancing unit 12. The chemical monitor, control and alarm may, for example, monitor the pH, osmolarity, electrolyte component, carbohydrate component, amino acid component, or other components of the nutrient emulsion to ensure that the nutrient input stream falls within preselected stream characteristics. In the event that these characteristics do not fall within the preselected range, the alarm for unit 42 may sound and/or may disable the system to thereby prevent further injection of nutrient input stream into the cerebrospinal pathway.

Finally, an oxygen/carbon dioxide monitor, control and alarm unit 36 is provided which continuously monitors the oxygen and carbon dioxide contents of the nutrient input stream, which controls the oxygenation unit 16, and which sounds an alarm in the event that the oxygen or carbon dioxide concentrations do not fall within preselected ranges. It is anticipated that each of units 36–42 may provide continuous displays of the information monitored from the nutrient input stream, and may, if desired, enable back-up units which either manually or automatically may supplement or replace the functions of units 12–18 in the event that those units are not functioning to produce a nutrient input stream within the desired ranges. For example, it is anticipated that a manual or battery operated pump, oxygenator, filter, and pressure and flow rate adjustments will be provided to enable emergency operation of the system, since continual nutrient flow is lifesaving for the devitalized portion of the treated organ.

The preferred nutrient emulsion of the present invention is comprised of carefully formulated components which, to the extent possible while maintaining desired therapeutic activity, mimic the physical and chemical characteristics of natural cerebrospinal fluid. Generally, tissues and cells will not fair well if exposed to large volumes of non-physiologic ionic solutions. Accordingly, it has been recognized that appropriate electrolyte compositions at the tissue level are indispensable when it is considered that the circulatory method of the present invention would otherwise result in the washing and the dilution of electrolytes from the region even after short terms of circulation, to the detriment of cell membrane functions. Accordingly, in accordance with the preferred embodiment of the present invention, sodium, potassium, calcium, magnesium, and chloride ions are carefully balanced in the nutrient emulsion of the present invention to thereby create, to the degree possible, normal extra-cellular compositions. The present invention also provides a non-aqueous oxygen transfer component for selectively combining with oxygen and for transferring oxygen to the tissues to be treated. Numerous compounds are known to the art which are characterized by having a high solvent property for oxygen, carbon dioxide, and other gases. The preferred non-aqueous oxygen transfer component of the preferred nutrient liquid should exhibit when so charged, oxygen vapor pressure ranges of above 400, and preferably 600, Torr. Such oxygen transfer components should similarly not have in themselves high vapor pressures which would boil at body temperatures, nor have viscosities which are difficult if not impossible to emulsify. Generally, the preferred compounds for use as non-aqueous oxygen transfer components are fluorocarbon polymers, such as perfluorocarbons, perfluorinated alkyl polyethers, fluoroethers, fluoroamines, etc. While compounds within these groups range in molecular weight from 250 to 7000, their selection for use as non-aqueous transport components are based upon the combination of features of the proper vapor pressure, molecular weight, viscosity, emulsifiability, emulsion-stability and tissue distribution. One such fluorocarbon which has been found to be particularly suited for the non-aqueous oxygen transport component of the preferred nutrient liquid is a compound sold by the 3-M Corporation under the trademark "FC-80". FC-80 has an oxygen solubility coefficient $ScO_2$ of 0.45 of ml $O^22$/ml at $pO_2$ of 760 Torr. See Navari et al., Res. Exp. Med., 170:169-180 (1977), which paper is specifically incorporated by reference as if fully set forth herein. It should be noted that whole blood under the same circumstances contains 0.23 ml $O_2$/ml. The FC-80$ScO_2$ is linear from 760 to 200 Torr but declines quite rapidly below the lower level. The high oxygen diffusion coefficient ($5.71/10^{-5}$ centimeters squared per second) indicates more than adequate FC-gas in a physiologic sense. Similar studies concerning $CO_2$ solubility and diffusion indicate that absorption and release are described by a straight line function. From these observations, metabolic tissue $CO_2$ accumulations should theoretically be easily removed by fluorocarbon solutions administered through a circulatory method.

Not only do fluorocarbons possess these unique physical gaseous properties but they are for the most part non-toxic. The main acute toxicity has been found to reside in free fluoride ion accumulation which occurs mainly from sonication. See, Clark et al., Fed. Proc., 34:1468-1477 (1979). The free ion can, however, be removed by repetitive dialysis and the emulsion thereby rendered physiologically acceptable. Accordingly, the preferred embodiment nutrient liquid of the present invention, which has been dialysized and filtered through a milipore filter, has evidenced no toxicity either in short term or long term use during circulation through cerebrospinal pathways of animals. One chief advantage of the CSF circulation route is that most or all the nutrient liquid can be removed by washing at the time of treatment termination. In this way long term cellular retention as previously noted for liver and reticuloendothelial cells in vascular circulations of oxygenating liquids may be avoided.

In the preferred embodiment nutrient liquid of the present invention, an emulsification component is provided for permitting the emulsification of the nutrient component with the oxygen transfer component of that liquid. The best currently available material for this purpose is believed to be block polyme polyols, which are known to the art as "pluronics", of which, pluronic F68 has proven to be a most efficient emulsifying agent. As used in a nutrient liquid as described more fully hereinafter, the toxicity from such a pluronic detergent is negligible. At the present time, however, it is anticipated that other emulsification components which will permit the non-aqueous transfer component of the nutrient liquid to become soluble with respect to the aqueous nutrient component of the nutrient liquid may be utilized to provide solutions which have adequate physiologic perimeters. Such other means of solubilizing fluorocarbons includes the formation of miceles, etc.

In the preparation of the preferred nutrient liquid, an important factor in producing an acceptable nutrient liquid is the achievement of an acceptable final osmotic pressure. The osmotic pressure of the nutrient liquid will depend upon the amount of the emulsification component, the particle size of the fluorocarbon, and the ionic composition of the aqueous nutrient component. In accordance with the preferred method of preparing the nutrient liquid of the present invention, toxic emulsification components should be removed by dialysis. Fluorocarbon particle size will be controlled by sonification time and filtering, while the ionic composition of the aqueous nutrient component will be carefully adjusted to produce a nutrient liquid possessing desired osmic characteristics. If desired, a final osmic tuning may be accomplished in accordance with the method of the present invention by adding ascorbic acid to the nutrient liquid.

In order to provide fully successful treatment of ischemic tissues, it is desirable to provide nutrient liquid for circulation around those tissues which will compensate for relative or complete deficiencies of blood transport metabolites. In addition to oxygen, other tissue metabolic requirements include glucose, amino acids, ions, hormones, vitamins, etc. While in temporary treatment conditions, it may be suitable to temporarily omit one or more vitamin, hormone, ion, or amino acid, for prolonged treatment and to produce the most desirable results, it is preferred to provide substantially all of the above mentioned metabolites in the preferred nutrient liquid. It is at least desirable to provide in the nutrient liquid all components necessary to support aerobic metabolism which will be available within the medium for use at cellular levels. Glucose deprivation of central nervous system tissue causes a serious cellular metabolic deficiency, as does the same degree of oxygen deficiency. Accordingly, by providing a total and finely adjusted mixture that has all the necessary components for total cell survival, an extremely efficient and therapeutic liquid material is provided which is ideal for circulation through the cerebrospinal pathways.

In order to illustrate the preferred method and composition of such an oxygen-nutrient material, the following example is provided:

EXAMPLE 1

Under conditions of replacing blood borne materials by perfusion all nutrients necessary for aerobic metabolism must be available within the medium for immediate use at cellular levels. As far as the central nervous system is concerned, glucose deprivation causes as serious a cellular metabolic deficiency as does the equivalency of oxygen lack. To achieve the desired ends we have added all known essential nutrients to the FC (fluorocarbon) emulsion. FC itself thereby serves the purpose of a gas transport system while the aqueous emulsion phase contains an array of cellular metabolic essentials. The total and finally adjusted mixture has all the necessary ingredients for total cell survival. The combination material is referred to as an oxygen-nutrient formula (Ox—N), or oxygenated nutrient emulsion.

Method and composition Preparation of Oxygen-Nutrient Material

1. Reagents (A) 5% Commercial grade Pluronic F68 (Basic Wynadotte).

(B) 20% W/V FC-80 (3M Corporation).

(C) Synthetic C.S.F.
  Sodium Chloride—7.3 gm/L
  Potassium Chloride—300 mg/L
  Calcium Chloride (dehyd)—200 mg/L
  Magnesium sulfate—300 mg/L
  Sodium Phosphate (hepta)—200 mg/L
  Sodium Bicarbonate—190 mg/L
  Adjust the pH to between 7.380–7.420 with 10% Ascorbic Acid (D) Bacitracin Inj. 50,000 u/vial (Pharmach) reconstitute with 10 ml saline to give a concentration of 5000 u/ml. Use 0.2 ml for each liter of perfusate to obtain a concentration of 1,000 units per liter of perfusate.

(E) Essential Amino Acids (Pool) (Sigma)
  D-Glutamic Acid—11.8 mg
  L-Glutamine—730.0 mg
  DL-Serine—26.3 mg
  D-Threonine—30.0 mg
  D-Lysine—38.8 mg
  D-Valine—19.0 mg
  D-Leucine—14.0 mg
  DL-Isoleucine—13.0 mg
  D-Phenylalanine—15.0 mg
  DL-Tyrosine—14.0mg
  D-Methionine—4.5 mg
  Before oxygenating the fluorocarbon emulsion add 9.8* mg. Amino Acid and 200 mg Dextrose for each 100 ml of emulsion.

*Siegel et al. pp. 297.

(F) Steroid (Methylprednisolone sodium succinate 125 mgs. The UpJohn Company). Reconstitute the steroid with 2 ml of dilutent to obtain a concentration of 62.5 mg/ml. Add 0.5 ml of this mixture to each liter of emulsion before oxygenation (31.2 mg/L).

(G) 1 N NaOH

2. Materials (A) Sonifier Cell Disruptor (Branson) Model W185D (B) Waring Blender for mechanical dispension of Pluronic Acid.

(C) Dialyzer tubing ⅞ in. (22 mm) (Thomas). It is necessary to dialyze the emulsion to remove fluoride ions as well as other low molecular weight contaminants.

(D) Whatman Filter Paper #1 (46×57) (Thomas) The emulsion should be filtered to remove particles originating from disrupted carbon skeletons of fluorocarbon during sonication.

(E) 0.8 micron filter unit (Thomas) Sterilization is accomplished by filtering the emulsion through a micro filter.

(F) $CO_2$ tank (Welders Supply Company) $CO_2$ is used as a defoaming agent while sonicating.

(G) 100% $O_2$ tank (Welders Supply Company) for saturating perfusate.

(H) Sterile Culture Flasks (Thomas) for storing perfusate.

(I) Gas Dispersion Tubes (Fisher Scientific Company) for equilibrating the emulsion with $O_2$.

(J) Aspiratory Bottle (Thomas)
  a. 250 ml capacity-cut off 2½" from the neck with a glass cutter in order to accommodate the macrotip for sonification.

| b. 500 ml capacity | for equilibration of the emulsion with 100% $O_2$. |
|---|---|
| 1000 ml capacity | |

(K) K50 Extension tubing (storeroom) Capacity approximately 2.1 ml length 50.7 centimeters (20 in.)

(L) Circulating Pump (M) Sonification Assembly
  a. Fill a container with crushed ice; one that will allow drainage of the water as the ice melts (a fish tank will do).
  b. On the serrated outlet near the bottom of the aspiratory bottle connect seven lengths (140 in) of K50 extension tubing. Place the bottle in the ice bath and connect the tubing to the circulating pump.
  c. Place the precooled Pluronic acid in the aspirator bottle. Drape and return extension tubing from the pump over the side of the bottle. Drape the tubes from the $CO_2$ tank over the side of the bottle and bubble slowly. Carefully lower the macrotip into the solution and start sonification.

3. Method 20% FC-80 (5% Pluronic (F68)) (w/v)

A. Place 25 gms of F68+250 ml of artificial C.S.F. in a Waring blender and blend at a high speed for 2 minutes. The solution will become very foamy. For best results the solution should be refrigerated overnight before using. This allows the head of foam to settle and precools the solution to the proper temperature for sonification.

B. Place the precooled Pluronic acid solution in the aspirator bottle. Turn on Sonifier. With a Pasteur pipette add 58.8 mls (100 gm) of FC-80 over a 30 minute period sonifying throughout. Once added allow the mixture to sonicate for 45 minutes. Be sure that the temperature does not exceed 20° C. Cut dialyzer tubing that has been presoaked in artificial C.S.F. into 60-inch strips. Fill each strip half full with the mixture. Place strips in containers filled with approximately 1000 ml, of artificial C.S.F. Refrigerate and allow to dialize for 48 hours. The dialyzing solution should be changed every twelve hours, and the amulsion checked and transferred to additional tubing since the volume is considerably increased during dialysis.

D. After dialysis filter the solution through Whatman #1 filter paper, then take the total volume. 25 gm of pluronic acid and 58.8 ml of FC-80 should yield between 500 and 750 ml of emulsion. The former volume represents 20% FC-80 and 5% F68 w/v ratio. The emission should be kept in an ice bath while processing.

E. Add bacitracin to the emulsion. The pH at this point should be between 6.5 and 6.8.

F. It is necessary to adjust the electrolytes at this stage. Unadjusted electrolytes:
  Na—127
  K=5
  Cl=26
  $CO_2$=1.5
  Osmolarity=271

It is necessary to add 696 mg Na Cl/L of emulsion in order to normalize the electrolytes.

Adjusted electrolytes:
Na=131
K=3.8
Cl=130
$CO_2$=3
Osmolarity=303

G. Using 1.0 N NaOH adjust the pH to between 7.380 and 7.420, then check the osmolarity. (Range 298-317).

H. Sterilize the emulsion by filtering through 0.8 micron filter. The emulsion can be frozen at −20° C. and is stable for several months.

4. Immediately Before Using Emulsion

A. Add:
Glucose: 0.8-2.5 gm/L
Amino Acid: 0.098 gm/l
Steroid 31.2 mg/L

B. Warm the emulsion to 37° C. and equilibrate with 100% $O_2$ using a gas dispersion tube for 30 minutes to obtain a $pO_2$ of between 580-660.

C. A typical batch of FC-80 emulsion shows the following properties:
Na=131 meg/L
K=3.8 meg/L
Cl=130 meg/L
$CO_2$=3 meg/L
Glucose=186 mg.%
Osmolarity=311 mOsM

| Gas Characteristics After Oxygen Equilibration | | |
|---|---|---|
| | Unsaturated | Saturated |
| pH | 7.231 | 7.342 |
| $pCO_2$ | 3.7 | 5.7 |
| $pO_2$ | 190 | 640 |

In order to provide an indication of efficacy of the preferred treatment methods, the following examples are provided:

EXAMPLE 2

For reasons of simplicity and reproducability a model continually in use in applicant's laboratory has been employed. Osteholm, J. L.; *Pathophysiology of Spinal Cord Injury*, C. C. Thomas, Springfield Ill. (1978). Extensive experience with spinal cord injury in terms of standardization, quantitative histological studies, regional blood flow and biochemical parameters suggested these procedures. A primary pathophysiologic event in that model has been determined to be discrete regional ischemia. A microcirculatory flow failure within the injured region has been documented by many study techniques including microangiography, distribution of intravascular paticulate mateials, hydrogen-platinum flow studies, regional isotopic techniques and lactate accumulation. Recent $C^{14}$ antipyrine microregional blood flow studies conducted in applicant's laboratory have accurately delineated the magnitude of ischemia in the injured cord. Within one hour the regional grey matter flow drops from the control of 44 cc/m100 gm/min to only 2 cc/100 gm/min. The white matter is also ischemic. Blood flows in these regions are depressed from 15 cc/100 gm/min to 1-2 cc/100 gm/min. The white matter is also ischemic. Blood flows in these regions are depressed from 15 cc/100 gm/min to 1-2 cc/100 gm/min.

From these observations, standardized spinal cord injury causes a restricted ischemic lesion which can be easily studied and quantitated. In this rigid system, therapeutic treatment effects are readily detected by comparison with our extensive untreated injury data. It should be noted here that the mechanical injury forces used in these experiments are substantially above saturation and all wounded animals are rendered permanently paraplegic.

Circulation Experiments

Experiments were carried out by continuously injecting either saline or Ox-N emulsion saturated with $O_2$ at 1 atm into the distal subarachnoid spinal space. The outflow (withdrawal) of the diagnostic fluid was at the cisterna magna. Infusions were begun immediately after severe wounding. An infusion rate of 3 ml/minute was easily achieved, and this rate was maintained for two hours.

Oxygen

Prior to lumbar spinal infusion we were able to develop $pO_2$ tensions of 535±89 mm $O_2$ in the Ox—N emulsion by simply bubbling 100% oxygen through the solution. Upon exit at the cisterna magna after traversing the entire spinal subarachnoid space the $pO_2$ had fallen to 243±63. The oxygen difference between entering and exit was 292±63, or a 55% decline, which is statistically significant at the P=<0.001 level. This finding indicates a rapid $pO_2$ exchange during the thirty seconds or less transit time. For various technical reasons our initial $pO_2$ was lower than can be achieved under idealized circumstances. More recently it has been possible to regularly attain $pO_2$ of 650 torr. It is postulated that even better experimental results might obtain under conditions of higher $O_2$ tension.

Carbon Dioxide

FC-80 is an efficient $CO_2$ exchange and transport agent, and the emulsion therefore easily extracts tissue $CO_2$. This is indicated by an initial emulsion $pCO_2$ of 2.7 torr which rose to 16.0 torr after the tissue perfusion contact. This represents a 593% increase in FC-80 $CO_2$ (P=<0.001). The emulsion also removes other acid metabolites since in some experiments the inherent buffering capacities were exceeded as the exit fluid pH exhibited a considerable depression toward the acid side (original pH 7.4, exit pH 7.0). This pH change exceeded any acid contribution by the collected $CO_2$, and amounted to 0.248 m mole lactate/hour.

A. Cross Sectional Area (Edema)

Frozen tissues were sectioned and stained (H & E, and acid phosphatase). The sections were evaluated by projection to 25X magnification and preselected lesion parameters measured by means of a compensating polar planimeter. There was considerable increase in the untreated injury cord cross sectional area (1280 mm²) which was significantly reduced in the OX—N experiments, (869 mm²). We have assumed that this substantial cross sectional cord area increase is caused by edema fluid. In the course of other experiments, the degree of edema appearance has been quantified. It was found that new water accumulation at those post injury times ranged from 25 to 40%. The absolute reduction in cross sectional area by the Ox—N treatment is significant at the P= <0.001 level.

Lesion Size

Using our standard sampling methodology which includes skip serial sections throughout the injury region, and analysis by quantification techniques, the degree of injury induced hemorrhagic necrosis can be determined. With the perfected injury system the lesion size at any time point can be reliably predicted. The effects of saline and Ox—N circulations upon lesion size were compared to each other and to our established untreated values. The results are summarized in Table I:

TABLE I

| | LESION SIZE 2 Hour Injuries | | |
|---|---|---|---|
| | % Grey | % White | % Total |
| Standard Injury (No Infusion) | 79.5 ± 16% SD | 30.1 ± 9% SD | 39.5 ± 10% SD |
| Saline Circulation | 78.3 ± 15% SD | 25.0 ± 14% SD | 34.4 ± 12% SD |
| Ox-N Circulation | 47.4* ± 17% SD | 12.8* ± 2% SD | 19.2* ± 10% SD |

Table I - Percentages are expressed in terms of total tissue area lesioned by hemorrhagic necrosis for grey, white or total cord area two hours after severe injury with the various treatments. (Statistical Significance $P = <*0.01$. The saline values are not significant)

The data indicates a highly significant degree of protection against injury lesions afforded by the Ox—N circulation treatments. The actual lesions are halved by the treatment and this remarkable stabilizing effect upon the important white matter tracts would be anticipated to substantially improve the final functional result attending severe spinal cord injury.

Anterior Horn Cells

A technique of counting the anterior horn cells which contain visible acid phosphatase histochemical reaction product has been developed in this laboratory. The procedure has been previously used to assess ischemic cellular effects in terms of cellular survival and/or lysis time.

From Table II it can be seen that untreated injury has a highly lethal effect upon anterior horn neurones. Within the two hour experimental time period, more than 97% of all cells at the injury center undergo cytoplasmic lysis. Ox—N infusions stabilized the injured cells as 60% of all neurones were protected from lysis.

TABLE II

| ANTERIOR HORN CELLS | |
|---|---|
| Control | 34 ± 2 (SD) |
| Injury | 2 ± 1.73* |
| Injury + Ox-N circulation | 21 ± 5.12** |

Table II - Number of anterior horn cells containing acid phosphatase reaction product within well defined cytoplasmic borders, (*statistical difference from control $P = <0.001$, **Difference from injury alone $P = <0.001$).

Spinal Cord Adenosine Triphosphate (ATP)

Biochemical ATP tissue determinations were undertaken to determine the metabolic oxidative state of injured spinal tissues. This metabolite was selected for study since it reflects the progress of normal oxidative metabolism. ATP levels fall very rapidly under sufficient hypoxic-ischemic conditions. Untreated injured cords have a 200% ATP decline in one minute. In the current experiments ATP levels would be expected to reflect (1) the cellular oxidative capability and (2) functional cellular viability. The latter aspect is especially important in terms of cellular integrity which was discussed in the preceeding section.

From Table III it can be seen that 2 hour injury causes a four and three fold drop in grey matter and white matter ATP respectively. This information amply supports other observations about the degree of regional cord tissue ischemia after impaction. ATP was found in significantly higher concentration in the Ox—N experiments than noted after saline circulation alone. The high energy compound suffered only a 30% fall from normal in the oxygenated perfusion group which contrasts vividly with the 300-400% loss found with the saline treatments.

TABLE III

| ATP LEVELS ($\mu$mol/gm) (2 hours post injury) | | | |
|---|---|---|---|
| | Injury & Saline | Injury & Ox-N | Control |
| Grey Matter | 0.46 | 1.24* | 1.88 |
| White Matter | 0.40 | 0.87* | 1.23 |

Table III - ATP tissue levels in control, saline and Ox-N injured cords. The difference between saline and Ox-N is significant *($P = <0.05$). Although not shown in the Table, the Ox-N treatments also statistically increase ATP in spinal cord regions directly above ($P = <0.05$) and below ($P = <0.001$) the injury site.

EXAMPLE 3

Cerebrovascular Ischemia

Initial studies have been conducted to determine the efficiency of Ox—N emulsions in protecting the brain against profound ischemia. We employed the cat brain and utilized right hemispheric regional vascular interruption so that the left cerebral hemisphere might serve as an internal control. The middle cerebral artery of cat is accessible through the bony orbit. It lies immediately above the optic nerve after the canal has been opened and can be identified with certainty in that position. Preliminary experiments determined that an inconstant cerebral field was devascularized by occluding the middle cerebral artery. It became apparent that collateral blood flow via the anterior and posterior cerebral arteries supplied some retrograde filling into the experimental region. This phenomenon could be largely prevented by concommittantly reducing the mean systemic blood pressure to 70 mmHg by external bleeding. Hemorrhagic hypotension plus middle cerebral artery occlusion yielded a reasonably constant ischemic cerebral lesion from animal to animal.

In that model either saline or Ox—N were circulated from the right cerebral ventricle to the cisterna magna at a rate of 3 ml/min. Cerebral tissues were harvested one hour after vascular occlusion by immediate immersion in liquid Freon. The tissues were sectioned in the frozen state and reacted with luciferin upon photographic film. A combination of high energy cellular metabolites plus luciferin react to emit visible light, which is recorded upon the film. Tissues removed from saline treated ischemic cerebral regions were uniquely devoid of phospholuminescence, while the opposite hemispheric demonstrated this reaction to a degree similar to that found in normal animals. Middle cerebral ischemic tissue samples from Ox—N treated animals contained sufficient high energy materials to demonstrate a positive histochemical high energy reaction one hour after vascular arrest.

EXAMPLE 4

Profound Spinal Cord Ischemia

The combined evidence from spinal cord injury and middle cerebral artery occlusion models demonstrate that the preferred oxygenated nutrient emulsion can be circulated to maintain cellular integrity and aerobic metabolism under the stress of profound regional ischemia. A third model was utilized to determine if vascular deprived neurones perfused via cerebrospinal fluid pathways with oxygenated-nutrient would continue to perform a physiologic function. A transthoracic aortic ligation just distal to the left subclavian effectively devascularizes the cervical, thoracic and lumbar cat spinal cord. In some examples the lower brain stem was also found ischemic by regional flow studies. The mid and lower thoracic cord are universally and profoundly blood deprived by this vascular interruption. Animals under light Ketamine anethesia were treated by circulating from the lumbar subarachnoid space to the cisterna magna with either saline or Ox—N solutions. Respiratory movements were evaluated in these experiments. The lungs were ventilated by positive presence respiration, but the mechanical movements are easily distinguished from neuromuscular respiratory contractions. This is especially so since for the most part the respiration and neuromuscular drive occur at separate times and are largely asynchronous. Following the aorta ligation all physiologic neuromuscular respiratory movements progressively diminished to total cessation after 5–10 minutes in the saline treated cats. The arrest obtains for intercostal muscles as well as diaphragmatic contractions. The Ox—N treated animals, on the other hand, continue to respire in an essentially normal neuromuscular sequence. The respiration, under those conditions, were often of irregular rate, diminished in amplitude, and showed some individual magnitude variations. The singular difference between saline and Ox—N circulations is the universal persistence of respiration in the latter group. It is also true that Ox—N sustained sufficient chest bellow movements so that if the chest were closed the respirations were clinically adequate to support life.

Conclusion

As seen from the above examples, and the foregoing description, circulation of the preferred embodiment nutrient liquid is capable of sustaining cellular integrity, aerobic metabolism and ongoing neuronal function. Even for neurons deep within the spinal cord (grey matter) the process has been successful in nurturing the ischemic neurons. The ability to sustain the central nervous system in a lethally ischemic field which persists for longer than a few minutes has never been accomplished before. The extra vascular pathway has not been employed as a global nutrient route prior to the present invention, nor has the combined use of oxygen rich emulsion which also contains other disclosed, novel components been known to the art.

As seen from the above experiments, the methods, compositions and system of the present invention are capable of providing substantial amounts of oxygen to neurologic tissues to be treated, while at the same time, removing the by-products of oxidated metabolism, including carbon dioxide, which have been found to exist in substantially higher concentrations in the exit, diagnostic fluid. Similarly, as discussed above, rapid, normally lethal, lyses of anterior horn cells is readily preventable through the treatment of the present invention, protecting at least 60% of the cells through this modality. Similarly, high energy phosphate metabolism utilizing both oxygen and glucose is maintained at substantial levels. Accordingly, the methodology of the present invention represents a substantial advance in the treatment of central nervous system tissue. Prior to this invention there was no available method to sustain central nervous system tissues after a few minutes of profound ischemic insult. This invention should revolutionize the therapeutic capabilities by providing therapeutic approaches for stroke, brain injury, vasospasm, senility, tumors, coma, spinal cord injury, ischemia, vasospasm, and central nervous system poisoning.

What is claimed is:

1. A method of diagnosing the condition of suspected hypoxic-ischemic central nervous sytem tissue of a mammal, comprising:
    (a) providing an oxygenated fluorocarbon emulsion synthetic spinal fluid;
    (b) injecting said synthetic spinal fluid into at least a first portion of the cerebrospinal pathway of said mammal to contact said tissue to become a diagnostic fluid;
    (c) withdrawing said diagnostic fluid from a second portion of said pathway to create a circulation of said fluid through at least a portion of said pathway;
    (d) monitoring the composition of said diagnostic fluid; and
    (e) comparing constituents of said fluid for at least a selected difference in the compositions of said synthetic spinal and diagnostic fluids;

whereby said selected differences in said compositions are at least diagnostic of the condition of said suspected hypoxic-ischemic tissue disposed along said portion of said cerebrospinal pathway.

2. The invention of claim 1 wherein said selected difference is a difference in oxygen content.

3. The invention of claim 1 wherein said selected difference is a difference in lactic acid concentration.

4. The invention of claim 1 wherein said selected difference is a difference in carbon dioxide concentration.

5. The invention of claim 1 wherein said selected difference is a difference in ammonia concentration.

6. The invention of claim 1 wherein said selected difference is a difference in enzyme content.

7. The invention of claim 1 wherein said difference is a difference in pH.

8. The invention of claim 1 wherein said difference is a difference in GABA.

9. The invention of claim 1 wherein said difference is a difference in microorganism content.

10. The invention of claim 9 wherein said microorganism content is a bacterial content.

11. The invention of claim 1 wherein said difference is a difference in ion concentration.

12. The invention of claim 11 wherein said ion concentration difference is a sodium ion concentration difference.

13. The invention of claim 11 wherein said difference is the difference in the concentration of potassium ions.

14. The invention of claim 1 wherein said difference is a difference in amino acid concentration.

15. The invention of claim 1 wherein said difference is a difference in concentration of malignant cells.

16. The invention of claim 1 wherein said difference is a difference in concentration of myelin fragments.

17. The invention of claim 1 wherein said difference is a difference in identifiable cellular materials.

18. The invention of claim 1 wherein said difference is a difference in concentration of identifiable cellular organelles.

19. The invention of claim 1 wherein said difference is a difference in protein.

20. The invention of claim 1 wherein said difference is a difference in fats.

21. The invention of claim 1 wherein said difference is a difference in fat content.

22. The invention of claim 1 wherein said difference is a difference in RNA content.

23. The invention of claim 1 wherein said difference is a difference in DNA content.

24. The invention of claim 1 wherein said difference is a difference in cellular metabolic products.

25. The invention of claim 1 wherein said difference is a difference in metabolite content.

26. The invention of claim 1 wherein said difference is a difference in neurotransmitter content.

* * * * *

UNITED STATES PATENT AND TRADEMARK OFFICE
CERTIFICATE OF CORRECTION

PATENT NO. : 4,445,514
DATED : May 1, 1984
INVENTOR(S) : OSTERHOLM

It is certified that error appears in the above-identified patent and that said Letters Patent are hereby corrected as shown below:

Column 9, line 47, please delete "inut" and substitute therefor --input--.

Column 14, line 50, please delete "amulsion" and substitute therefor --emulsion--.

Column 15, line 58, please delete "paticulate mateials" and substitute therefor --particulate materials--.

Signed and Sealed this

Eleventh Day of December 1984

[SEAL]

Attest:

Attesting Officer

GERALD J. MOSSINGHOFF

Commissioner of Patents and Trademarks